(12) United States Patent
Kim et al.

(10) Patent No.: US 9,008,383 B2
(45) Date of Patent: Apr. 14, 2015

(54) ENHANCING QUALITY OF ULTRASOUND IMAGE IN ULTRASOUND SYSTEM

(75) Inventors: Jeong Sik Kim, Seoul (KR); Song Yi Han, Seoul (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 605 days.

(21) Appl. No.: 13/290,691

(22) Filed: Nov. 7, 2011

(65) Prior Publication Data

US 2012/0114210 A1   May 10, 2012

(30) Foreign Application Priority Data

Nov. 10, 2010 (KR) .................. 10-2010-0111371
Nov. 10, 2010 (KR) .................. 10-2010-0111372

(51) Int. Cl.
| | |
|---|---|
| G06K 9/00 | (2006.01) |
| G01S 7/52 | (2006.01) |
| G06T 5/20 | (2006.01) |
| G06T 5/00 | (2006.01) |
| G01S 15/89 | (2006.01) |

(52) U.S. Cl.
CPC .......... *G01S 7/52046* (2013.01); *G01S 7/52077* (2013.01); *G01S 15/8995* (2013.01); *G06T 5/20* (2013.01); *G06T 5/003* (2013.01); *G06T 2207/10132* (2013.01)

(58) Field of Classification Search
CPC . G01S 7/52046; G01S 7/52077; G06T 5/003; G06T 2207/10132; A61B 8/5269
USPC .......... 382/128, 255, 260, 261, 263; 600/437, 600/443; 367/7
See application file for complete search history.

(56) References Cited

U.S. PATENT DOCUMENTS

| | | | |
|---|---|---|---|
| 5,339,282 A | 8/1994 | Kuhn et al. | 367/7 |
| 5,862,269 A * | 1/1999 | Cohen et al. | 382/304 |
| 8,157,737 B2 * | 4/2012 | Zhang et al. | 600/443 |

(Continued)

FOREIGN PATENT DOCUMENTS

| | | | | |
|---|---|---|---|---|
| JP | 2000-237187 A | 9/2000 | ............... | A61B 8/00 |
| JP | 2003-190157 A | 7/2003 | ............... | A61B 8/00 |
| KR | 10-2008-0060625 A | 7/2008 | ............... | A61B 8/13 |

OTHER PUBLICATIONS

Partial European Search Report issued in European Patent Application No. EP 13158377.5 dated May 16, 2013.

(Continued)

*Primary Examiner* — Andrew W Johns
(74) *Attorney, Agent, or Firm* — McDermott Will & Emery LLP

(57) ABSTRACT

There are provided embodiments for enhancing the quality of an ultrasound image are disclosed. In one embodiment, by way of non-limiting example, an ultrasound system comprises: an ultrasound data acquisition unit configured to acquire ultrasound data corresponding to at least one ultrasound image; a storage unit for storing at least one beam profile indicating a spreading degree of an ultrasound beam according to depth based on at least one focusing point; and a processing unit configured to set an amount of blurring corresponding to spreading of the ultrasound beam according to the depth based on the at least one beam profile, and perform a filtering process for compensating the blurring by the spreading of the ultrasound beam based on the ultrasound data and the amount of blurring to enhance quality of the at least one ultrasound image.

19 Claims, 14 Drawing Sheets

(56) References Cited

U.S. PATENT DOCUMENTS

| | | | |
|---|---|---|---|
| 8,221,322 B2* | 7/2012 | Wang et al. | 600/437 |
| 2002/0085237 A1 | 7/2002 | Bradburn | 358/3.27 |
| 2009/0143680 A1 | 6/2009 | Yao et al. | 600/443 |
| 2010/0049042 A1 | 2/2010 | Azuma | 600/437 |

OTHER PUBLICATIONS

E.E. Hundt et al., "Digital Processing of Ultrasonic Data by Deconvolution," IEEE Transactions on Sonics and Ultrasonics, vol. SU-27, No. 5, Sep. 1980, pp. 249-252.
European Office Action issued in European Patent Application No. 11 187 789.0 dated May 31, 2013.
Extended European Search Report issued in European Patent Application No. EP 13158377.5 dated Dec. 3, 2013.
Korean Office Action issued in Korean Application No. 10-2010-0111372 dated Apr. 29, 2013.
Korean Notice of Allowance, w/ English translation thereof, issued in Korean Patent Application No. KR 10-2010-0111372 dated Sep. 5, 2013.
European Search Report issued in European Patent Application No. 11187789.0 dated Jul. 19, 2012.
European Search Report issued in European Patent Application No. 11187789.0 dated Mar. 28, 2012.
Buzug, T. "Advances in Medical Engineering". pp. 157-162.
Hewener, H.J. "Deconvolution of freehand ultrasound data using improved reconstruction techniques in consideration of ultrasound point spread functions". IFMBE proceedings 22, pp. 436-439, 2008.
Taxt, T., et al. "Noise Robust Two-Dimensional Blind Deconvolution of Ultrasound Images". IEEE Ultrasonics Symposium, pp. 1465-1469, 1997.
Vollmann W. "Resolution Enhancement of Ultrasonic B-Scan Images by Deconvolution". IEEE Transactions on Sonics and Ultrasonics, vol. SU-29, No. 2, Mar. 1982, pp. 78-83.
Jensen, AJ, et al. "Calculation of Pressure Fields from Arbitrarily Shaped, Apodized, and Excited Ultrasound Transducers". IEEE Transactions on Ultrasonics. vol. 39, No. 2, Mar. 1992, pp. 262-267.
http://mi.eng.cam.ac.uk/research/projects/Deconvolution_Of 3D_Ultrasound/H. Shin et al., "Sensitivity to Point-Spread Function Parameters in Medical Ultrasound Image Deconvolution", PACS: 43.80.Vj; 43.60.Fg; 87.63.dh, Apr. 30, 2008, pp. 1-22.

* cited by examiner

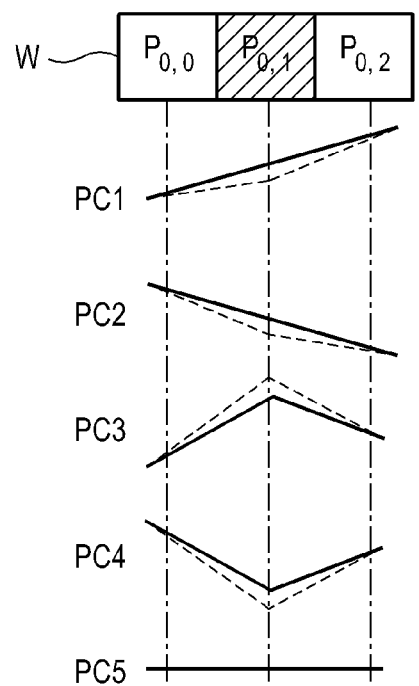

Point target

——————— FIRST ULTRSOUND IMAGE
—·—·—·— SECOND ULTRASOUND IMAGE
- - - - - - - THIRD ULTRASOUND IMAGE
—··—··—··— ULTRASOUND SPATIAL COMPOUND IMAGE

ENHANCING QUALITY OF ULTRASOUND IMAGE IN ULTRASOUND SYSTEM

CROSS-REFERENCE TO RELATED APPLICATIONS

The present application claims priority from Korean Patent Application Nos. 10-2010-0111371 and 10-2010-0111372 filed on Nov. 10, 2010, the entire subject matters of which are incorporated herein by reference.

TECHNICAL FIELD

The present disclosure generally relates to ultrasound systems, and more particularly to enhancing quality of an ultrasound image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two-dimensional or three-dimensional ultrasound images of internal features of a target object (e.g., human organs).

The ultrasound system may transmit ultrasound signals to a living body by using an ultrasound probe. The living body includes a target object (e.g., a heart, a fetus, etc.). The ultrasound signals from the ultrasound probe are transmitted as an ultrasound beam to the living body. The ultrasound system may further receive ultrasound signals (i.e., ultrasound echo signals) from the living body. The ultrasound system may also form an ultrasound image of the living body based on the received ultrasound echo signals.

Generally, as the depth becomes shallower or deeper based on a focusing point FP, the spreading of the ultrasound beam becomes serious. An artifact that a size of point targets seems differently in an ultrasound image even for an identical size of the point targets PT in the living body. That is, a blurring which makes the ultrasound image unclear may occur. Accordingly, this presents a problem since the ultrasound image corresponding to the original shape and size of the target object cannot be provided.

SUMMARY

There are provided embodiments for enhancing the quality of an ultrasound image are disclosed herein.

In one embodiment, by way of non-limiting example, an ultrasound system comprises: an ultrasound data acquisition unit configured to acquire ultrasound data corresponding to at least one ultrasound image; a storage unit for storing at least one beam profile indicating a spreading degree of an ultrasound beam according to depth based on at least one focusing point; and a processing unit configured to set an amount of blurring corresponding to spreading of the ultrasound beam according to the depth based on the at least one beam profile, and perform a filtering process for compensating the blurring by the spreading of the ultrasound beam based on the ultrasound data and the amount of blurring to enhance quality of the at least one ultrasound image.

In another embodiment, there is provided a method of enhancing the quality of an ultrasound image, comprising: a) acquiring ultrasound data corresponding to at least one ultrasound image; b) setting an amount of blurring corresponding to spreading of the ultrasound beam by using at least one beam profile indicating a spreading degree of an ultrasound beam according to the depth based on at least one focusing point; and c) performing a filtering process for compensating the blurring by the spreading of the ultrasound beam based on the ultrasound data and the amount of blurring to enhance quality of the at least one ultrasound image.

This summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 8 is a schematic diagram showing an example of a window in the second embodiment.

FIG. 9 is a schematic diagram showing an example of a change of pixel values in the second embodiment.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

First Embodiment

Figure 1:
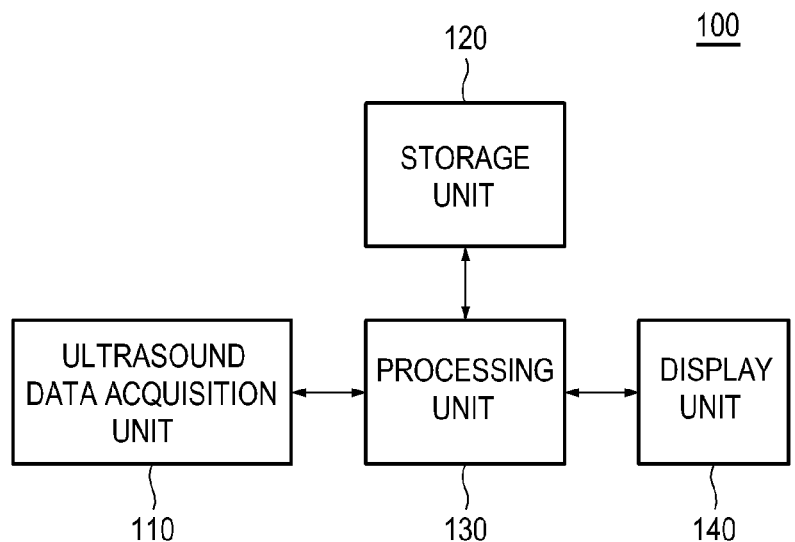
FIG. 1 is a block diagram showing an ultrasound system in accordance with a first embodiment.

Referring to FIG. 1, an ultrasound system 100 in accordance with a first embodiment is shown. As depicted therein, the ultrasound system 100 may include an ultrasound data acquisition unit 110.

The ultrasound data acquisition unit 110 may be configured to transmit ultrasound signals to a living body. The living body may include target objects (e.g., a heart, a fetus and the like). The ultrasound data acquisition unit 110 may be further configured to receive ultrasound signals (i.e., ultrasound echo signals) from the living body to acquire ultrasound data.

Figure 2:
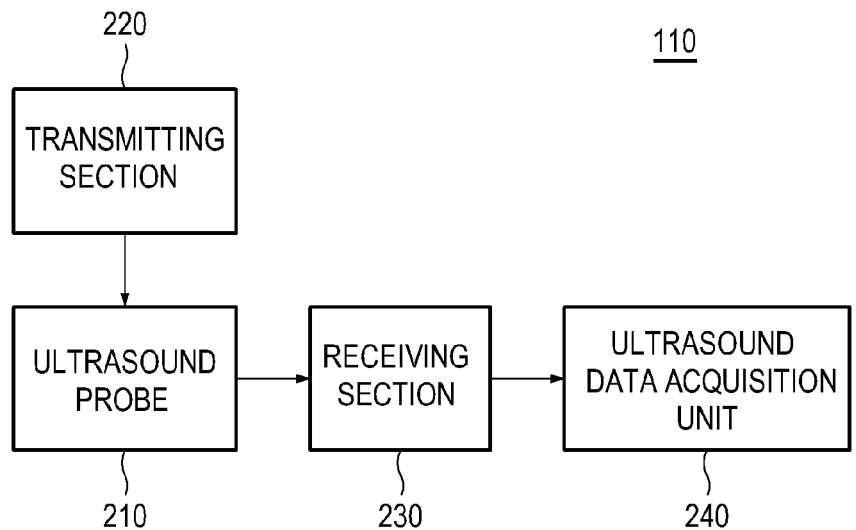
FIG. 2 is a block diagram showing an ultrasound data acquisition unit in accordance with the first embodiment.

FIG. 2 is a block diagram showing the ultrasound data acquisition unit in accordance with the first embodiment. Referring to FIG. 2, the ultrasound data acquisition unit 110 may include an ultrasound probe 210.

The ultrasound probe 210 may include a plurality of elements (not shown) for reciprocally converting between ultrasound signals and electrical signals. The ultrasound probe 210 may be configured to transmit ultrasound signals to the living body. The ultrasound probe 210 may be further configured to receive ultrasound echo signals from the living body to output received signals. The received signals may be analog signals. The ultrasound probe 210 may include a convex probe, a linear probe and the like.

The ultrasound data acquisition unit 110 may further include a transmitting section 220. The transmitting section 220 may be configured to control the transmission of the ultrasound signals. The transmitting section 220 may be further configured to generate electrical signals ("transmitting signals") for obtaining an ultrasound image in consideration of the elements and focusing points. As such, the ultrasound probe 210 may be configured to convert the transmitting signals into the ultrasound signals, transmit the ultrasound signals to the living body and receive the ultrasound echo signals from the living body to thereby output the received signals. The ultrasound image may include a brightness mode image. However, it should be noted herein that the ultrasound image may not be limited thereto. The transmitting section 220 may include a transmitting signal generating section (not shown), a transmitting delay time information memory (not shown), a transmitting beam former (not shown) and the like.

The ultrasound data acquisition unit 110 may further include a receiving section 230. The receiving section 230 may be configured to convert the received signals provided from the ultrasound probe 210 into digital signals. The receiving section 230 may be further configured to apply delays to the digital signals in consideration of the elements and the focusing points to thereby output digital receive-focused signals. The receiving section 230 may include an analog-to-digital converter (not shown), a receiving delay time information memory (not shown), a receiving beam former (not shown) and the like.

The ultrasound data acquisition unit 110 may further include an ultrasound data forming section 240. The ultrasound data forming section 240 may be configured to form ultrasound data corresponding to the ultrasound image based on the digital receive-focused signals provided from the receiving section 230. The ultrasound data may include radio frequency data. However, it should be noted herein that the ultrasound data may not be limited thereto. The ultrasound data forming section 240 may be further configured to perform signal processing (e.g., gain control, etc) upon the digital receive-focused signals.

Figure 3:
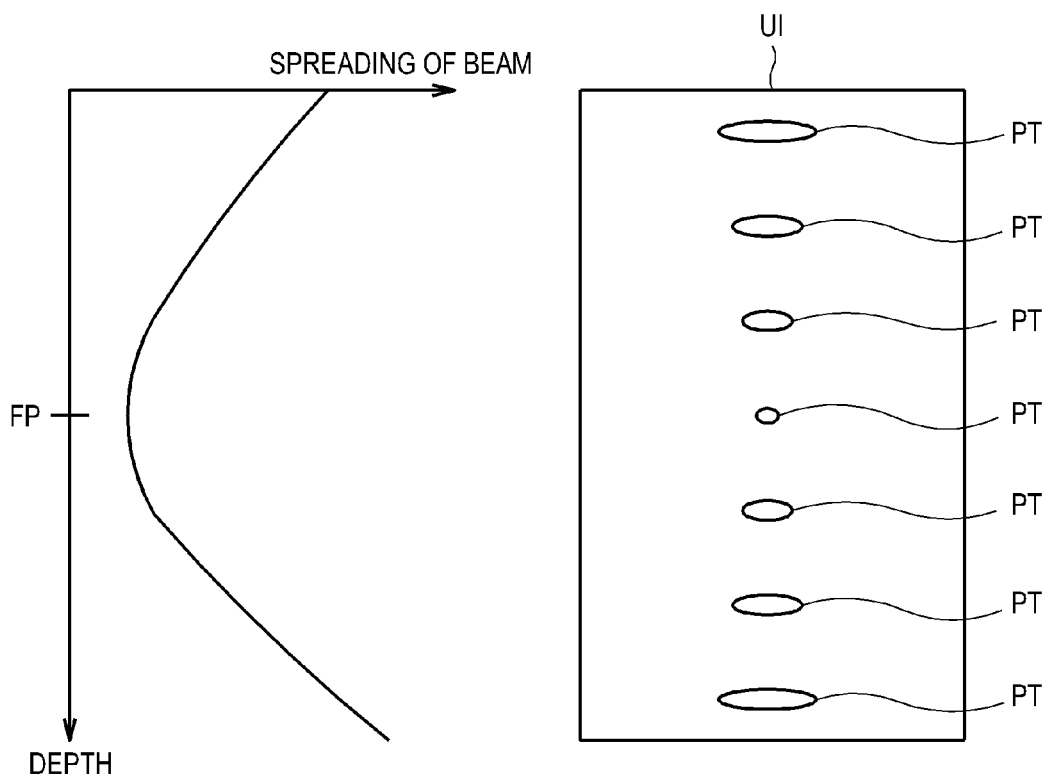
FIG. 3 is a schematic diagram showing an example of a beam profile in accordance with the first embodiment.

Referring back to FIG. 1, the ultrasound system 100 may further include a storage unit 120. The storage unit 120 may store at least one beam profile corresponding to at least one focusing point. The beam profile may indicate a spreading degree of an ultrasound beam according to depth. In the embodiment, the storage unit 120 may store a plurality of beam profiles corresponding to a plurality of focusing points. For example, the storage unit 120 may store the beam profile indicating the spread degree of the ultrasound beam according to the depth based on a focusing point FP, as shown in FIG. 3. As the depth goes shallower or deeper based on the focusing point FP, the spreading of the ultrasound beam becomes serious. Thus, an artifact that a size of point targets appears differently in an ultrasound image even for an identical size of the point targets PT in the living body, as shown in FIG. 3. That is, a blurring which makes the ultrasound image unclear may occur.

Although it has been described that the storage unit 120 stores the beam profile, the storage unit 120 may further store an amount of blurring corresponding to the beam profile.

The ultrasound system 100 may further include a processing unit 130 in communication with the ultrasound data acquisition unit 110 and the storage unit 120. The processing unit 130 may be configured to set the amount of blurring corresponding to the spreading of the ultrasound beam according to the depth for the ultrasound image, based on the beam profile. The processing unit 130 may be further configured to perform a filtering process for compensating the blurring by the spreading of the ultrasound beam, based on the ultrasound data and the amount of blurring. The processing unit 130 may include a central processing unit, a microprocessor, a graphic processing unit and the like.

Figure 4:
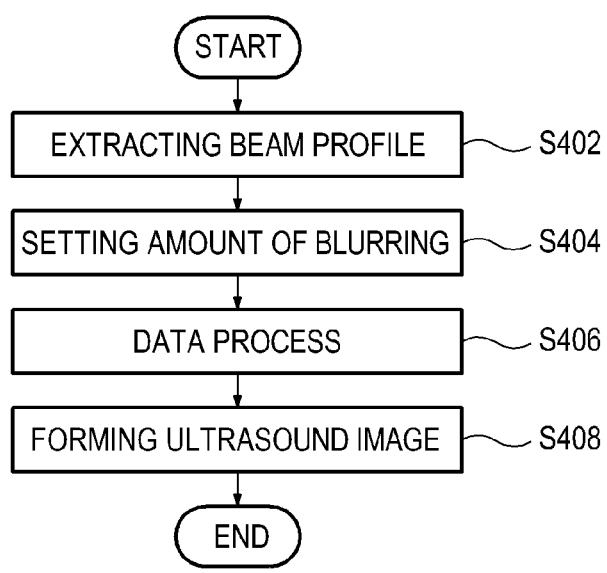
FIG. 4 is a flow chart showing a process of enhancing quality of the ultrasound image based on a beam profile in accordance with the first embodiment.

FIG. 4 is a flow chart showing a process of enhancing quality of the ultrasound image based on the beam profile in accordance with the first embodiment. The processing 130 may be configured to retrieve the storage unit 120 to extract a beam profile corresponding to a focusing point, at step S402 in FIG. 4.

Figure 5:
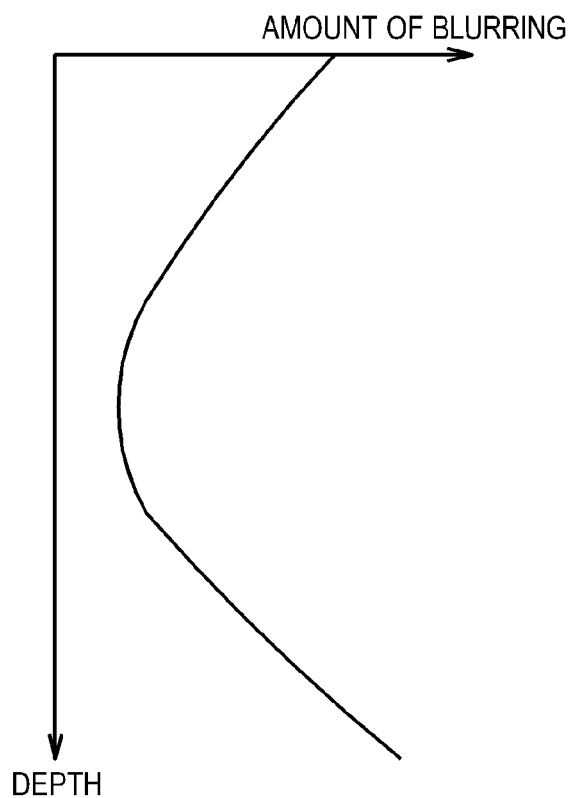
FIG. 5 is a schematic diagram showing an example of an amount of blurring in accordance with the first embodiment.

The processing unit 130 may be configured to set the amount of blurring corresponding to the spreading of the ultrasound beam according to depth for the ultrasound image, based on the extracted beam profile, at step S404 in FIG. 4. In the embodiment, the processing unit 130 may set the amount of blurring corresponding to the spreading of the ultrasound beam according to the depth based on the focusing point FP for the ultrasound image, based on the beam profile, as shown in FIG. 5. The amount of blurring may be equal to the beam profile. That is, the amount of blurring may be equal to the spreading degree of the ultrasound beam.

Figure 6:
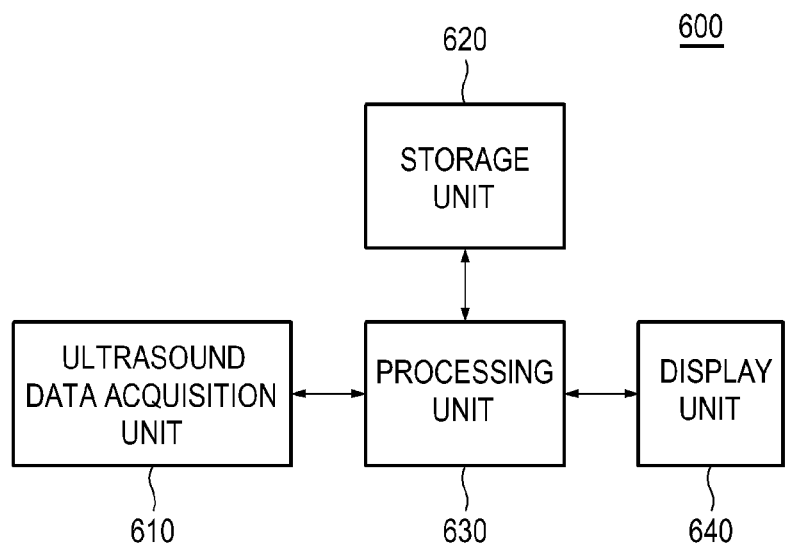
FIG. 6 is a block diagram showing an ultrasound system in accordance with a second embodiment.

The processing unit 130 may be configured to perform a data process (i.e., filtering process) for compensating the blurring by the spreading of the ultrasound beam upon the ultrasound data provided from the ultrasound data acquisition unit 110 based on the amount of blurring, at step S406 in FIG. 6. In the embodiment, the data process may include a blind deconversion, an inverse filtering and the like.

The processing unit 130 may be configured to form the ultrasound image based on the data-processed ultrasound data, at step S408 in FIG. 4. The methods of forming the ultrasound image are well known in the art. Thus, they have not been described in detail so as not to unnecessarily obscure the present invention.

Referring back to FIG. 1, the ultrasound system 100 may further include a display unit 140. The display unit 140 may be configured to display the ultrasound image formed by the processing unit 130.

Second Embodiment

FIG. 6 is a block diagram showing an ultrasound system in accordance with a second embodiment. Referring to FIG. 6, the ultrasound system 600 may include an ultrasound data acquisition unit 610.

The ultrasound data acquisition unit 610 may be configured to transmit the ultrasound signals to the living body. The ultrasound data acquisition unit 610 may be further configured to receive the ultrasound echo signals from the living body to acquire ultrasound data. The ultrasound data acquisition unit 610 in the second embodiment is similar to the ultrasound data acquisition unit 110 in the first embodiment. Thus, it has not been described in detail.

The ultrasound system 600 may further include a storage unit 620. The storage unit 620 may store at least one beam profile corresponding to at least one focusing point. The storage unit 620 in the second embodiment is similar to the storage unit 120 in the first embodiment. Thus, it has not been described in detail.

The ultrasound system 600 may further include a processing unit 630 in communication with the ultrasound data acquisition unit 610 and the storage unit 620. The processing unit 630 may be configured to set the amount of blurring corresponding to the spreading of the ultrasound beam according to the depth for the ultrasound image, based on the beam profile. The processing unit 630 may be further configured to perform the filtering process for compensating the blurring by the spreading of the ultrasound beam, based on the ultrasound data and the amount of blurring. The processing unit 630 may include a central processing unit, a microprocessor, a graphic processing unit and the like.

Figure 7:
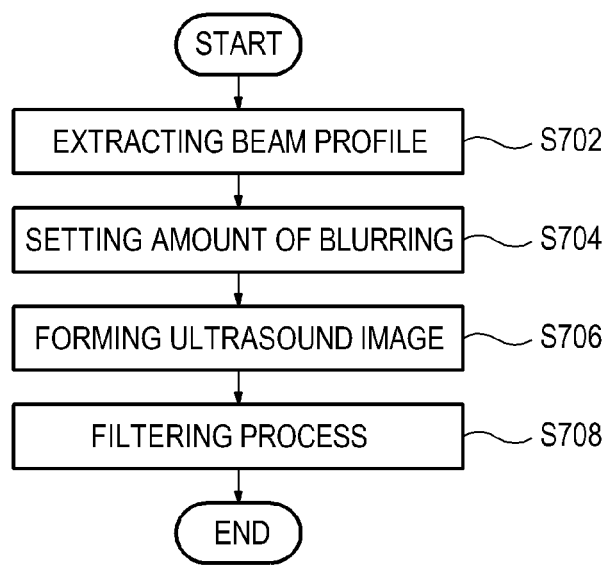
FIG. 7 is a flow chart showing a process of enhancing quality of an ultrasound image based on a beam profile in accordance with the second embodiment.

FIG. 7 is a flow chart showing a process of enhancing quality of the ultrasound image in accordance with the second embodiment. The processing unit 630 may be configured to retrieve the storage unit 620 to extract a beam profile corresponding to a focusing point, at step S702 in FIG. 7.

The processing unit 630 may be configured to set the amount of blurring corresponding to the spreading of the ultrasound beam according to the depth for the ultrasound image, based on the extracted beam profile, at step S704 in FIG. 7. The methods of setting the amount of blurring in the second embodiment are similar to the methods of setting the amount of blurring in the first embodiment. Thus, they have not been described in detail.

The processing unit 630 may be configured to form the ultrasound image based on the ultrasound data provided from the ultrasound data acquisition unit 610, at step S706 in FIG. 7. The methods of forming the ultrasound image are well known in the art. Thus, they have not been described in detail so as not to unnecessarily obscure the present invention.

The processing unit 630 may be configured to perform the filtering process for compensating the blurring by the spreading of the ultrasound beam upon the ultrasound image, based on the amount of blurring, at step S708 in FIG. 7.

In the embodiment, the processing unit 630 may set a window W based on a pixel $P_{0,1}$ of the ultrasound image UI, as shown in FIG. 8. The window W may have a predetermined size. For example, the window W may have a size of 1×3. The processing unit 630 may further detect pixel values (i.e., brightness values) of pixels $P_{0,0}$, $P_{0,1}$ and $P_{0,2}$ corresponding to the window W. The processing unit 630 may further compare the pixel values to detect a change of the pixel values of the pixels corresponding to the window W. If it is determined that the pixel values increase (solid line of PC1) or decreases (solid line of PC2) as shown in FIG. 9, the processing unit 630 may perform the filtering process (dotted line of PC1 or PC2) for decreasing the pixel value of the pixel $P_{0,1}$, based on the amount of blurring corresponding to the depth of the pixel $P_{0,1}$. Else, if it is determined that the pixel value of the pixel $P_{0,1}$ located on the center of the pixels $P_{0,0}$, $P_{0,1}$ and $P_{0,2}$ corresponding to the window W is a maximum value (solid line of PC3) as shown in FIG. 9, the processing unit 630 may perform the filtering process (dotted line of PC3) for increasing the pixel value of the pixel $P_{0,1}$, based on the amount of blurring corresponding to the depth of the pixel $P_{0,1}$. Else, if it is determined that the pixel value of the pixel $P_{0,1}$ located on the center of the pixels $P_{0,0}$, $P_{0,1}$ and $P_{0,2}$ corresponding to the window W is a minimum value (solid line of PC4) as shown in FIG. 9, the processing unit 630 may perform the filtering process (dotted line of PC4) for decreasing the pixel value of the pixel $P_{0,1}$, based on the amount of blurring corresponding to the depth of the pixel $P_{0,1}$. Else, if it is determined that the change of the pixel values is zero (PC5), that is, the pixel values of the pixels $P_{0,0}$, $P_{0,1}$ and $P_{0,2}$ corresponding to the window W are equal to one another as shown in FIG. 9, the processing unit 630 may not perform the filtering process upon the pixel $P_{0,1}$. The processing unit 630 may perform the above-described filtering process upon all pixels of the ultrasound image UI, while shifting the window W by one pixel.

Referring back to FIG. 6, the ultrasound system 600 further includes a display unit 640. The display unit 640 may be configured to display the ultrasound image formed by the processing unit 630.

Third Embodiment

Figure 10:
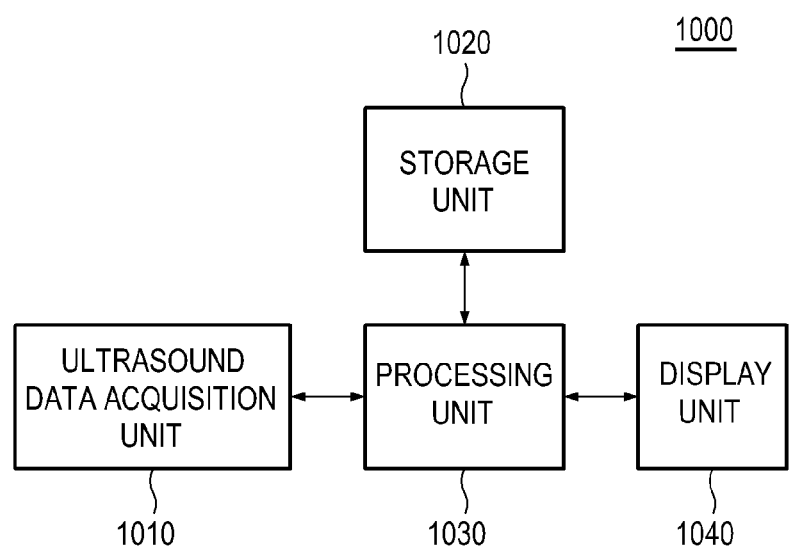
FIG. 10 is a block diagram showing an ultrasound system in accordance with a third embodiment.

FIG. 10 is a block diagram showing an ultrasound system in accordance with a third embodiment. Referring to FIG. 10, the ultrasound system 1000 may include an ultrasound data acquisition unit 1010.

The ultrasound data acquisition unit 1010 may be configured to transmit the ultrasound signals to the living body. The ultrasound data acquisition unit 1010 may be further configured to receive the ultrasound echo signals from the living body to acquire ultrasound data.

Figure 11:
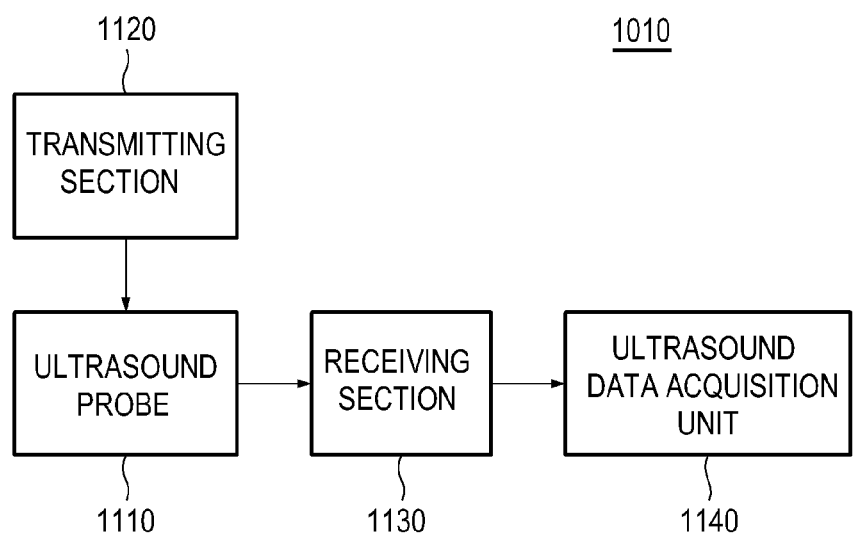
FIG. 11 is a block diagram showing an ultrasound data acquisition unit in accordance with the third embodiment.

FIG. 11 is a block diagram showing the ultrasound data acquisition unit in accordance with the third embodiment. Referring to FIG. 11, the ultrasound data acquisition unit 1010 may include an ultrasound probe 1110.

The ultrasound probe 11110 may include a plurality of elements (not shown) for reciprocally converting between ultrasound signals and electrical signals. The ultrasound probe 1110 may be configured to transmit the ultrasound signals to the living body. The ultrasound probe 1110 may be further configured to receive the ultrasound echo signals from the living body to output received signals. The received signals may be analog signals. The ultrasound probe 1110 may include a convex probe. However, it should be noted herein that the ultrasound probe 1110 may not be limited thereto.

The ultrasound data acquisition unit 1010 may further include a transmitting section 1120. The transmitting section 1120 may be configured to control the transmission of the ultrasound signals. The transmitting section 1120 may be further configured to generate electrical signals ("transmitting signals") for obtaining an ultrasound image in consideration of the elements, focusing points and steering angles. Thus, the ultrasound probe 1110 may be configured to convert the transmitting signals into the ultrasound signals, transmit the ultrasound signals to the living body and receive the ultrasound echo signals from the living body to thereby output the received signals. The ultrasound image may include a brightness mode image. However, it should be noted herein that the ultrasound image may not be limited thereto. The transmitting section 1120 may include a transmitting signal generating section (not shown), a transmitting delay time information memory (not shown), a transmitting beam former (not shown) and the like.

Figure 12:
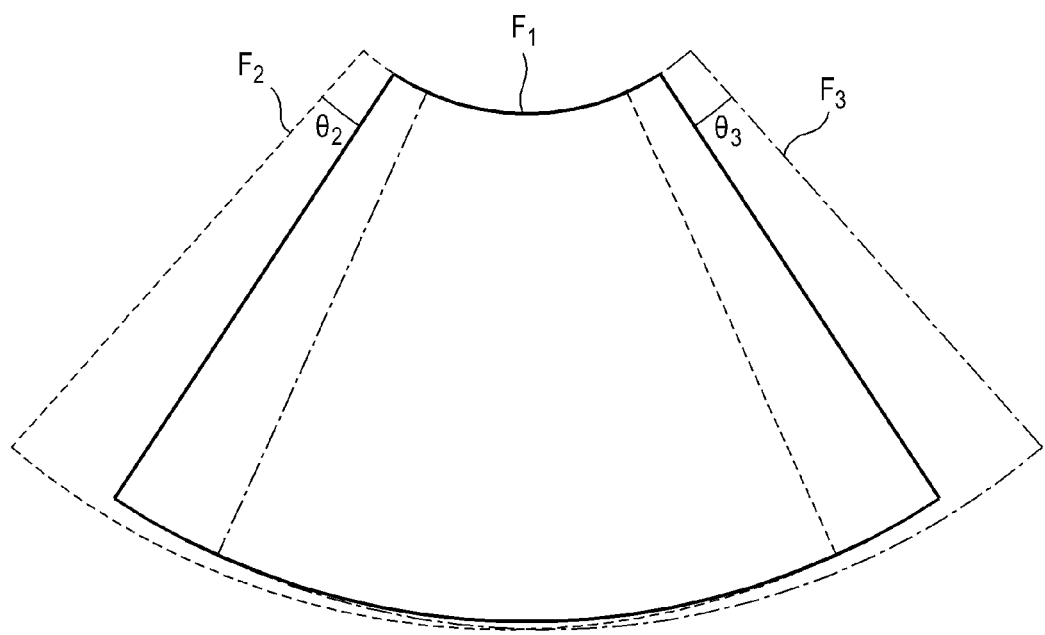
FIG. 12 is a schematic diagram showing an example of a plurality of ultrasound images corresponding to a plurality of steering angles.

In the embodiment, the transmitting section 1120 may form first transmitting signals for obtaining a first ultrasound image $F_1$ corresponding to a first steering angle of the scan-lines (not shown), as shown in FIG. 12. Thus, the ultrasound probe 1110 may convert the first transmitting signals into the ultrasound signals, transmit the ultrasound signals to the living body and receive the ultrasound echo signals from the living body to thereby output first received signals. The first steering angle may be 0°. However, it should be noted herein that the first steering angle may not be limited thereto. The transmitting section 1120 may further form second transmitting signals for obtaining a second ultrasound image $F_2$ corresponding to a second steering angle $\theta_2$ of the scan-lines, as shown in FIG. 12. Thus, the ultrasound probe 1110 may convert the second transmitting signals into the ultrasound signals, transmit the ultrasound signals to the living body and receive the ultrasound echo signals from the living body to thereby output second received signals. The transmitting section 1120 may further form third transmitting signals for obtaining a third ultrasound image $F_3$ corresponding to a third steering angle $\theta_3$ of the scan-lines, as shown in FIG. 12. Thus, the ultrasound probe 1110 may convert the third transmitting signals into the ultrasound signals, transmit the ultrasound signals to the living body and receive the ultrasound echo signals from the living body to thereby output third received signals.

The ultrasound data acquisition unit 1010 may further include a receiving section 1130. The receiving section 1130 may be configured to convert the received signals provided from the ultrasound probe 1110 into digital signals. The receiving section 1130 may be further configured to apply delays to the digital signals in consideration of the elements, the focusing points and the steering angles to thereby output digital receive-focused signals. The receiving section 1130 may include an analog-to-digital converter (not shown), a receiving delay time information memory (not shown), a receiving beam former (not shown) and the like.

In the embodiment, the receiving section 1130 may convert the first received signals into first digital signals. The receiving section 1130 may further apply delays to the first digital signals in consideration of the elements, the focusing points and the first steering angle to thereby output first digital receive-focused signals. The receiving section 1130 may further convert the second received signals into second digital signals. The receiving section 1130 may further apply delays to the second digital signals in consideration of the elements, the focusing points and the second steering angle to thereby output second digital receive-focused signals. The receiving section 1130 may further convert the third received signals into third digital signals. The receiving section 1130 may further apply delays to the third digital signals in consideration of the elements, the focusing points and the third steering angle to thereby output third digital receive-focused signals.

The ultrasound data acquisition unit 1010 may further include an ultrasound data forming section 1140. The ultrasound data forming section 1140 may be configured to form ultrasound data corresponding to the ultrasound image based on the digital receive-focused signals provided from the receiving section 1130. The ultrasound data may include radio frequency data. However, it should be noted herein that the ultrasound data may not be limited thereto. The ultrasound data forming section 1140 may be further configured to perform signal processing (e.g., gain control, etc) upon the digital receive-focused signals.

In the embodiment, the ultrasound data forming section 1140 may form first ultrasound data corresponding to the first ultrasound image $F_1$ of the first steering angle based on the first digital receive-focused signals provided from the receiving section 1130. The ultrasound data forming section 1140 may further form second ultrasound data corresponding to the second ultrasound image $F_2$ of the second steering angle $\theta_2$ based on the second digital receive-focused signals provided from the receiving section 1130. The ultrasound data forming section 1140 may further form third ultrasound data corresponding to the third ultrasound image $F_3$ of the third steering angle $\theta_3$ based on the third digital receive-focused signals provided from the receiving section 1130.

Although it is described that the ultrasound data corresponding to the ultrasound image of the three steering angles (i.e., first to third steering angles) are acquired, the steering angles are certainly not limited thereto.

Referring back to FIG. 10, the ultrasound system 1000 may further include a storage unit 1020. The storage unit 1020 may store at least one beam profile corresponding to at least one focusing point. The beam profile may indicate a spreading degree of an ultrasound beam according to depth. In the embodiment, the storage unit 1020 may store a plurality of beam profiles corresponding to a plurality of focusing points. The beam profile in the third embodiment is similar to the beam profile in the first embodiment. Thus, it has not been described in detail.

Figure 13:
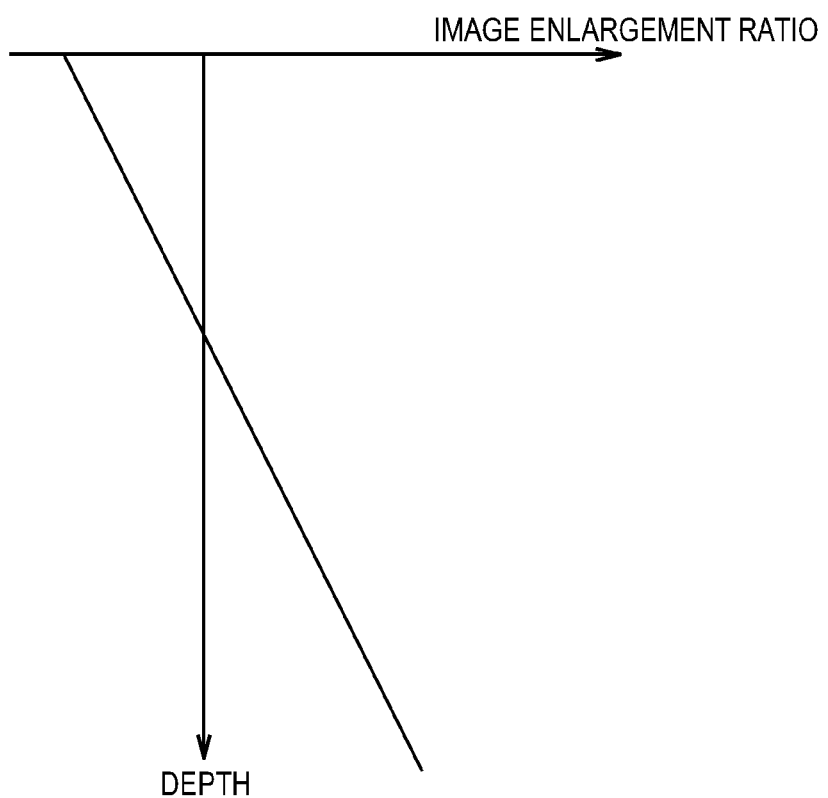
FIG. 13 is a schematic diagram showing an example of image enlargement ratio information in accordance with the third embodiment.

The storage unit 1020 may further store image enlargement ratio information. The image enlargement ratio information may indicate an ultrasound image enlargement ratio by a scan conversion, as shown in FIG. 13.

Although it has been described that the storage unit 1020 stores the beam profile and the image enlargement ratio information, the storage unit 1020 may further store an amount of blurring corresponding to the beam profile and the image enlargement ratio information.

The ultrasound system 1000 may further include a processing unit 1030 in communication with the ultrasound data acquisition unit 1010 and the storage unit 1020. The processing unit 1030 may be configured to set the amount of blurring corresponding to the spreading of the ultrasound beam and the scan conversion (i.e., image enlargement) according to the depth for the ultrasound images, based on the beam profile and the image enlargement ratio information. The processing unit 1030 may be further configured to perform a filtering process for compensating the blurring by the spreading of the ultrasound beam and the scan conversion, based on the ultrasound data and the amount of blurring. The processing unit 1030 may include a central processing unit, a microprocessor, a graphic processing unit and the like.

Figure 14:
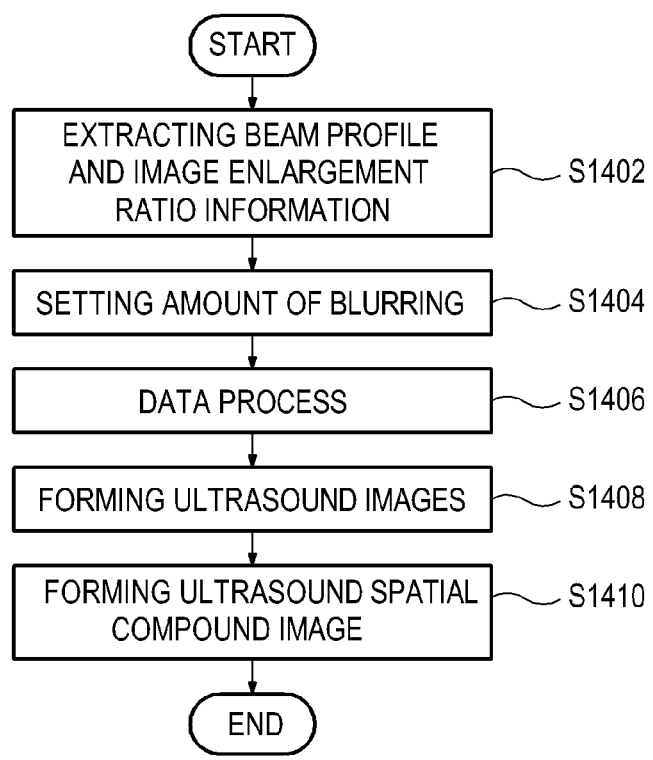
FIG. 14 is a flow chart showing a process of enhancing quality of an ultrasound image based on a beam profile and image enlargement ratio information in accordance with the third embodiment.

FIG. 14 is a flow chart showing a process of enhancing quality of an ultrasound image based on the beam profile and image enlargement ratio information in accordance with the third embodiment. The processing 1030 may be configured to retrieve the storage unit 1020 to extract a beam profile and image enlargement ratio information corresponding to a focusing point, at step S1402 in FIG. 14.

The processing unit 1030 may be configured to set the amount of blurring corresponding to the spreading of the ultrasound beam and the image enlargement according to the depth for the ultrasound images, based on the beam profile and the image enlargement ratio information, at step S1404 in FIG. 14.

Figure 15:
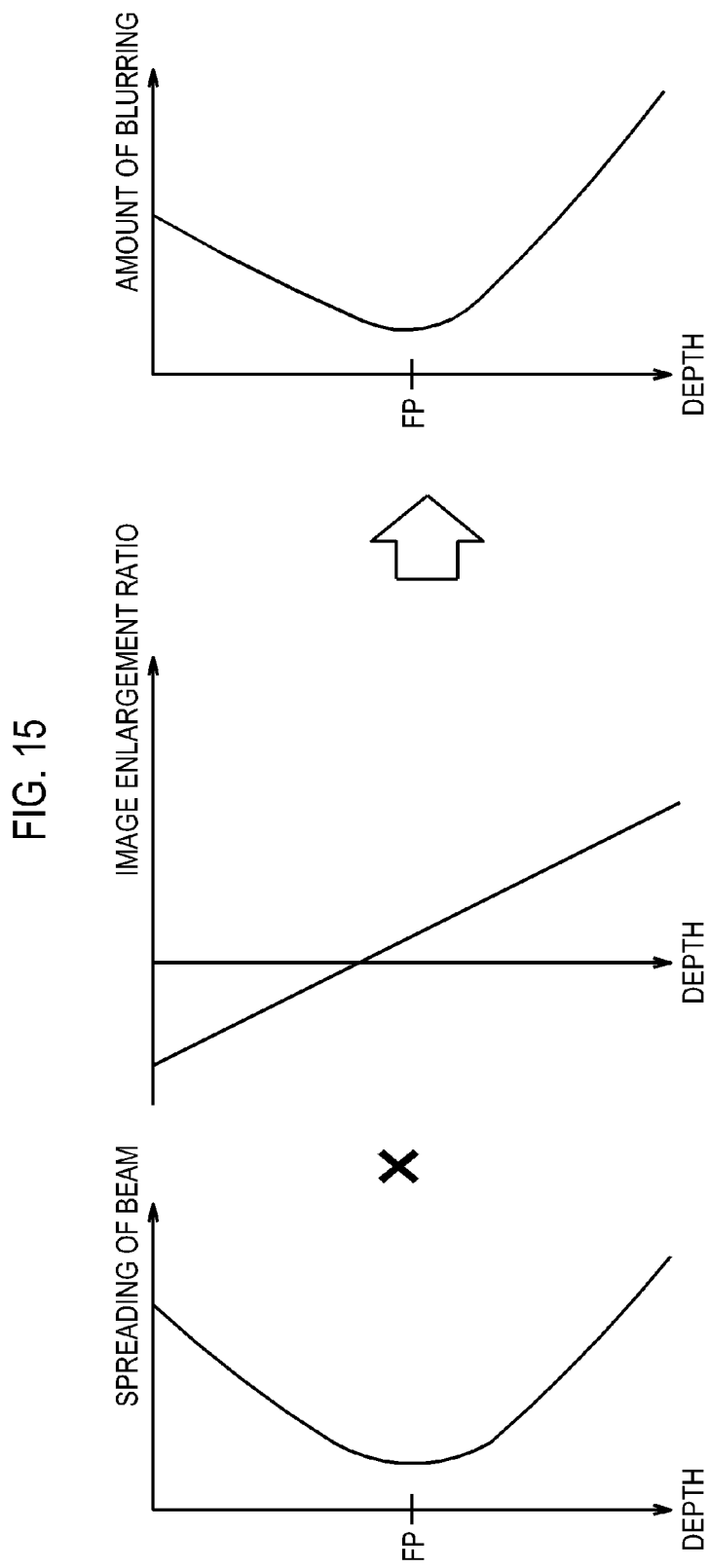
FIG. 15 is a schematic diagram showing an example of an amount of blurring in accordance with the third embodiment.

In the embodiment, the processing unit 1030 may multiply the beam profile with the image enlargement ratio information according to the depth to set the amount of blurring corresponding to the spreading of the ultrasound beam and the scan conversion, as shown in FIG. 15. Since the first to third ultrasound images $F_1$ to $F_3$ are only differently in terms of steering angles of the scan-lines and are identical in terms of the beam profile, the amount of blurring corresponding to the first to third ultrasound images $F_1$ to $F_3$ are the same. Thus, the processing unit 1030 may set a single amount of blurring for the first to third ultrasound images $F_1$ to $F_3$.

The processing unit 1030 may be configured to perform a data process (i.e., filtering process) for compensating the blurring by the spreading of the ultrasound beam and the scan conversion upon the ultrasound data provided from the ultrasound data acquisition unit 1010, based on the amount of blurring, at step S1406 in FIG. 14. The data process may include a blind deconversion, an inverse filtering and the like.

In the embodiment, the processing unit 1030 may perform the data process for compensating the blurring by the spread of the ultrasound beam and the scan conversion upon the ultrasound data corresponding to each of the first to third ultrasound images $F_1$ to $F_3$.

The processing unit 1030 may be configured to form the ultrasound images based on the data-processed ultrasound data, at step S1408 in FIG. 14. The methods of forming the ultrasound images are well known in the art. Thus, they have not been described in detail so as not to unnecessarily obscure the present invention.

The processing unit 1030 may be configured to perform the scan conversion upon the data-processed ultrasound data to form the ultrasound images corresponding to the steering angles, at step S1408 in FIG. 14.

The processing unit 1030 may be configured to perform a spatial compound upon the ultrasound images to form an ultrasound spatial compound image, at step S1410 in FIG. 14. The methods of forming the ultrasound spatial compound image are well known in the art. Thus, they have not been described in detail so as not to unnecessarily obscure the present invention.

Figure 16:
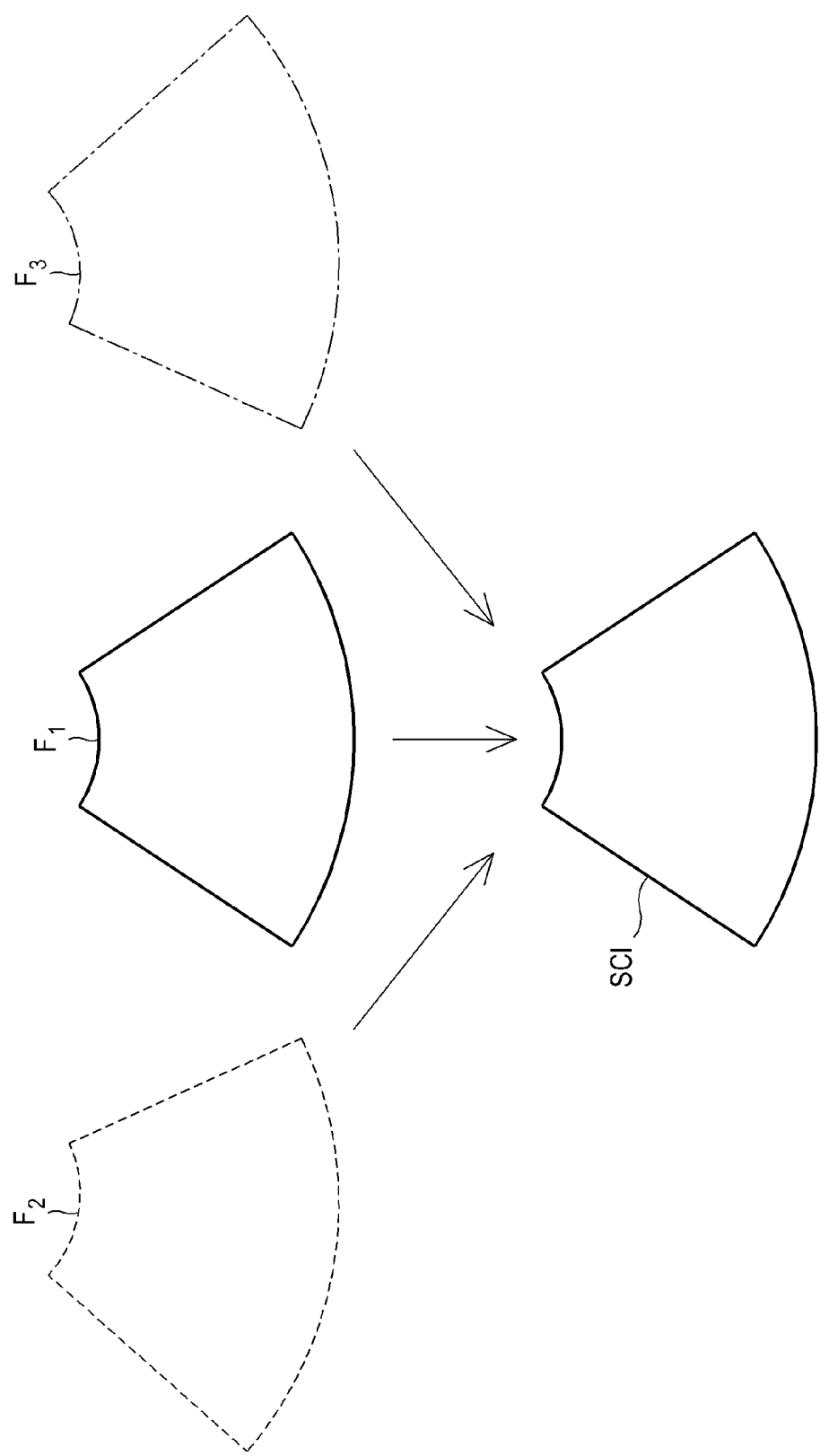
FIG. 16 is a schematic diagram showing an example of an ultrasound spatial compound image.

In the embodiment, the processing unit 1030 may form the first to third ultrasound images $F_1$ to $F_3$ based on the data-processed first to third ultrasound data, as shown in FIG. 16. The processing unit 1030 may further perform the spatial compound upon the first to third ultrasound images $F_1$ to $F_3$ to form the ultrasound spatial compound image SCI, as shown in FIG. 16.

Figure 17:
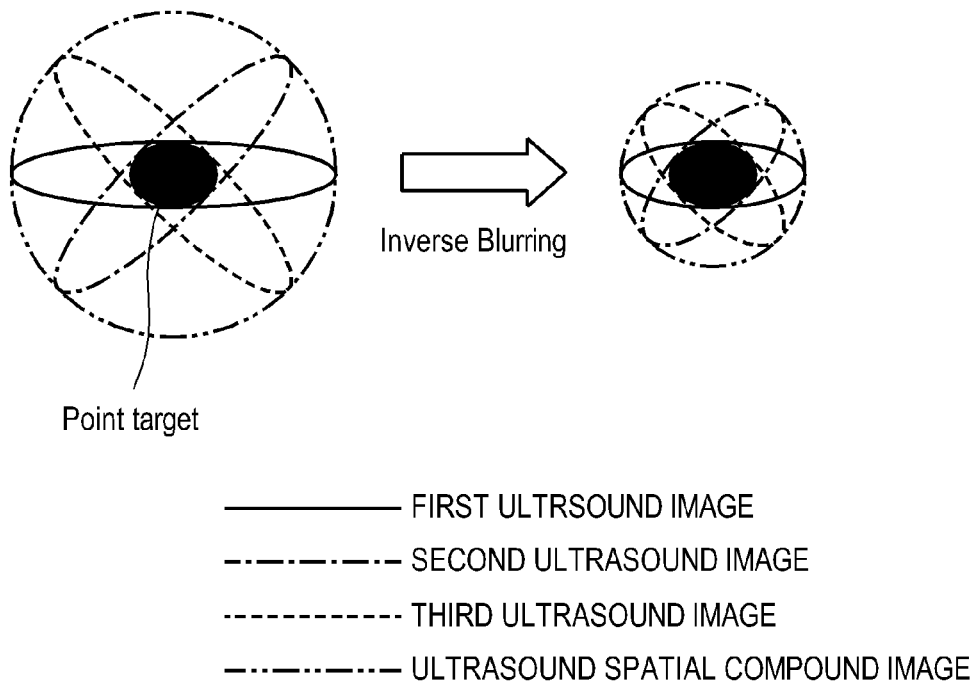
FIG. 17 is a schematic diagram showing an example of enhancing quality of the ultrasound spatial compound image by an inverse blurring process.

The size of the point target in the ultrasound spatial compound image is similar to the size of the target point, as performing the spatial compound upon the inverse blurring-processed ultrasound images to form the ultrasound spatial compound image, as shown in FIG. 17. Thus, the quality of the ultrasound spatial compound image may be enhanced.

Referring back to FIG. 10, the ultrasound system 1000 may further include a display unit 1040. The display unit 1040 may be configured to display the ultrasound spatial compound image formed by the processing unit 1030. The display unit 1040 may be further configured to display the ultrasound images formed by the processing unit 1030.

Fourth Embodiment

Figure 18:
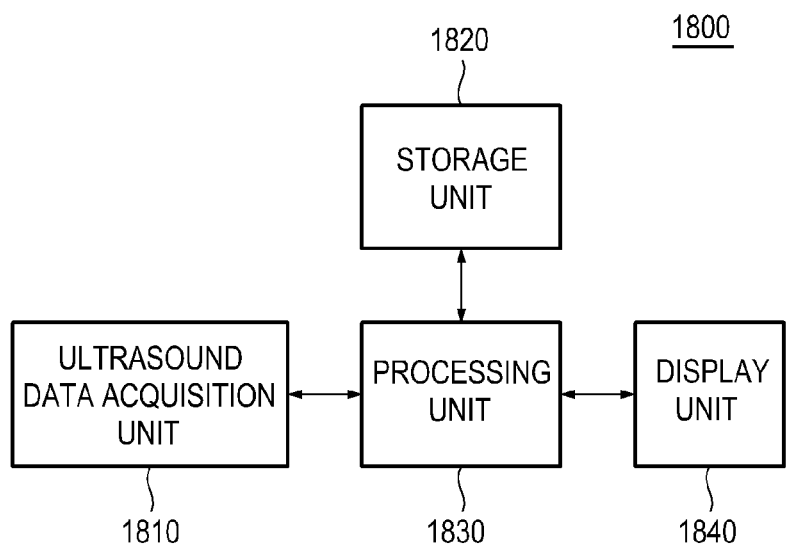
FIG. 18 is a block diagram showing an ultrasound system in accordance with a fourth embodiment.

FIG. 18 is a block diagram showing an ultrasound system in accordance with a fourth embodiment. Referring to FIG. 18, the ultrasound system 1800 may include an ultrasound data acquisition unit 1810.

The ultrasound data acquisition unit 1810 may be configured to transmit the ultrasound signals to the living body. The ultrasound data acquisition unit 1810 may be further configured to receive the ultrasound echo signals from the living body to acquire ultrasound data. The ultrasound data acquisition unit 1810 in the fourth embodiment is similar to the ultrasound data acquisition unit 1010 in the third embodiment. Thus, it has not been described in detail.

The ultrasound system 1800 may further include a storage unit 1820. The storage unit 1820 may store at least one beam profile corresponding to at least one focusing point. The storage unit 1820 may further store image enlargement ratio information indicating an ultrasound image enlargement ratio by a scan conversion. The storage unit 1802 in the fourth embodiment is similar to the storage unit 1020 in the third embodiment. Thus, it has not been described in detail.

The ultrasound system 1800 may further include a processing unit 1830 in communication with the ultrasound data acquisition unit 1810 and the storage unit 1820. The processing unit 1830 may be configured to set the amount of blurring corresponding to the spreading of the ultrasound beam and the scan conversion according to the depth for the ultrasound images, based on the beam profile and the image enlargement ratio information. The processing unit 1830 may be further configured to perform a filtering process for compensating the blurring by the spreading of the ultrasound beam and the scan conversion, based on the ultrasound data and the amount of blurring. The processing unit 1830 may include a central processing unit, a microprocessor, a graphic processing unit and the like.

Figure 19:
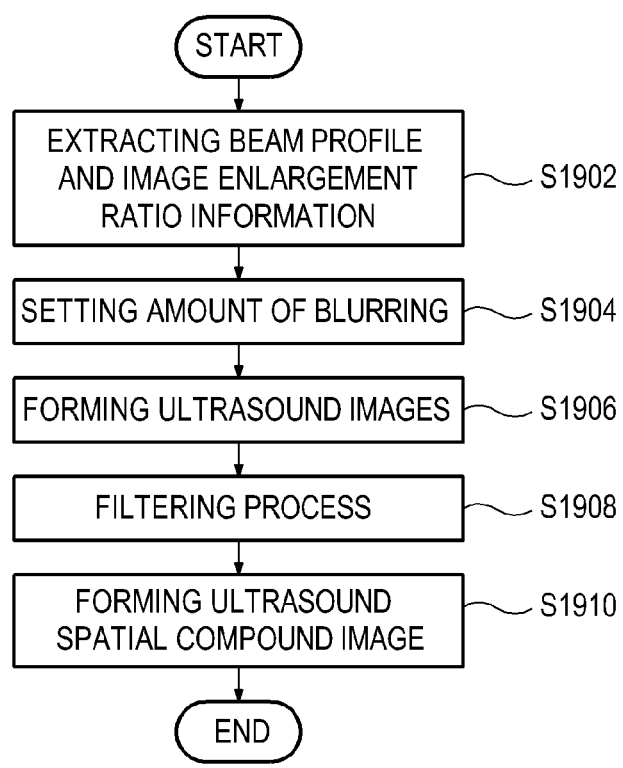
FIG. 19 is a flow chart showing a process of enhancing quality of an ultrasound image based on a beam profile and image enlargement ratio information in accordance with the fourth embodiment.

FIG. 19 is a flow chart showing a process of enhancing quality of the ultrasound image based on the beam profile and image enlargement ratio information in accordance with the fourth embodiment. The processing 1830 may be configured to retrieve the storage unit 1820 to extract a beam profile and image enlargement ratio information corresponding to a focusing point, at step S1902 in FIG. 19.

The processing unit 1830 may be configured to set the amount of blurring corresponding to the spreading of the ultrasound beam and the image enlargement according to the depth for the ultrasound image, based on the beam profile and the image enlarging ratio information, at step S1904 in FIG. 19. The methods of setting the amount of blurring in the fourth embodiment are similar to the methods of setting the amount of blurring in the third embodiment. Thus, they have not been described in detail.

The processing unit 1830 may be configured to perform the scan conversion upon the ultrasound data provided from the ultrasound data acquisition unit 1810 to form the ultrasound images corresponding to the steering angles, at step S1906 in FIG. 19.

The processing unit 1830 may be configured to perform a filtering process for compensating the blurring by the spreading of the ultrasound beam and the scan conversion upon the ultrasound images, based on the amount of blurring, at step S1908 in FIG. 19. The filtering process in the fourth embodiment is similar to the filtering process in the second embodiment. Thus, it has not been described in detail.

The processing unit 1830 may be configured to perform a spatial compound upon the filtering-processed ultrasound images to form an ultrasound spatial compound image, at step S1910 in FIG. 19. The methods of forming the ultrasound spatial compound image are well known in the art. Thus, they have not been described in detail so as not to unnecessarily obscure the present invention.

Referring back to FIG. 18, the ultrasound system 1800 may further include a display unit 1840. The display unit 1840 may be configured to display the ultrasound spatial compound image formed by the processing unit 1830. The display unit 1840 may be further configured to display the ultrasound images formed by the processing unit 1830.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
    an ultrasound data acquisition unit including an ultrasound probe and configured to acquire ultrasound data corresponding to at least one ultrasound image;
    a storage for storing a plurality of beam profiles respectively corresponding to a plurality of focusing points, each of the plurality of beam profiles indicating a spreading degree of an ultrasound beam according to depth based on the corresponding focusing point; and
    a processing unit including a microprocessor and configured to extract a beam profile corresponding to a focusing point among the plurality of beam profiles, set an amount of blurring corresponding to spreading of the ultrasound beam according to a depth for the at least one ultrasound image based on the extracted beam profile, the processing unit being further configured to perform a filtering process for compensating the blurring by the spreading of the ultrasound beam based on the ultrasound data and the set amount of blurring to enhance quality of the at least one ultrasound image.

2. The ultrasound system of claim 1, wherein the set amount of blurring is equal to the extracted beam profile.

3. The ultrasound system of claim 1, wherein the processing unit is configured to:
    perform the filtering process upon the ultrasound data based on the set amount of blurring; and
    form the at least one ultrasound image based on the filtering-processed ultrasound data.

4. The ultrasound system of claim 3, wherein the filtering process comprises a blind deconversion or an inverse filtering.

5. The ultrasound system of claim 1, wherein the processing unit is configured to:
    form the at least one ultrasound image based on the ultrasound data; and
    perform the filtering process upon the least one ultrasound image based on the set amount of blurring.

6. The ultrasound system of claim 5, wherein the processing unit is configured to:
    set a window having a predetermined size based on each of pixels for the at least one ultrasound image;
    detect pixel values of pixels corresponding to the window;
    compare the pixel values to detect a change of the pixel values of the pixels corresponding to the window; and
    perform the filtering process upon each of the pixels based on the change of the pixel values and the set amount of blurring.

7. The ultrasound system of claim 6, wherein the processing unit is configure to:
    when it is determined that the pixel values increase or decrease, perform the filtering process for decreasing the pixel values of the pixels based on the set amount of blurring corresponding to the depth of each of the pixels;
    when it is determined that the pixel value of the pixel located on the center of the window is a maximum value, perform the filtering process for increasing the pixel value of the pixel corresponding to the maximum value based on the set amount of blurring corresponding to the depth of the pixel corresponding to the maximum value; and
    when it is determined that the pixel value of the pixel located on the center of the window is a minimum value, perform the filtering process for decreasing the pixel value of the pixel corresponding to the minimum value based on set amount of blurring corresponding to the depth of the pixel corresponding to the minimum value.

8. The ultrasound system of claim 1, wherein the storage further stores image enlargement ratio information indicating an ultrasound image enlargement ratio by a scan conversion.

9. The ultrasound system of claim 8, wherein the processing unit is configured to set the amount of blurring corresponding to the spreading of the ultrasound beam and the scan conversion according to the depth for the at least ultrasound image based on the extracted beam profile and the image enlargement ratio information.

10. The ultrasound system of claim 9, wherein the processing unit is configured to multiply the extracted beam profile with the image enlargement ratio information according to the depth for the at least ultrasound image to set the amount of blurring.

11. A method for enhancing the quality of an ultrasound image, comprising:
    a) acquiring ultrasound data corresponding to at least one ultrasound image;
    b) storing a plurality of beam profiles respectively corresponding to a plurality of focusing points, each of the plurality of beam profiles indicating a spreading degree of an ultrasound beam according to depth based on the corresponding focusing point;
    c) extracting a beam profile corresponding to a focusing point among the plurality of beam profiles;
    d) setting an amount of blurring corresponding to spreading of the ultrasound beam according to a depth for the at least one ultrasound image based on the extracted beam profile and
    e) performing a filtering process for compensating the blurring by the spreading of the ultrasound beam based on the ultrasound data and the set amount of blurring to enhance quality of the at least one ultrasound image.

12. The method of claim 11, wherein the set amount of blurring is equal to the extracted beam profile.

13. The method of claim 11, wherein the step e) comprises:
    performing the filtering process upon the ultrasound data based on the set amount of blurring; and
    forming the at least one ultrasound image using the filtering-processed ultrasound data.

14. The method of claim 13, wherein the filtering process comprises a blind deconversion or an inverse filtering.

15. The method of claim 11, wherein the step e) comprises:
    forming the at least one ultrasound image based on the ultrasound data; and
    performing the filtering process upon the least one ultrasound image based on the set amount of blurring.

16. The method of claim 15, wherein the step e) comprises:
    e1) setting a window having a predetermined size based on each of pixels for the at least one ultrasound image;

e2) detecting pixel values of pixels corresponding to the window;
e3) comparing the pixel values to detect a change of the pixel values of the pixels corresponding to the window; and
e4) performing the filtering process upon each of the pixels based on the change of the pixel values and the set amount of blurring.

17. The method of claim 16, wherein the step e4) comprises:
when it is determined that the pixel values increase or decrease, performing the filtering process for decreasing the pixel values of the pixels based on the set amount of blurring corresponding to the depth of each of the pixels;
when it is determined that the pixel value of the pixel located on the center of the window is a maximum value, performing the filtering process for increasing the pixel value of the pixel corresponding to the maximum value based on the set amount of blurring corresponding to the depth of the pixel corresponding to the maximum value; and
when it is determined that the pixel value of the pixel located on the center of the window is a minimum value, performing the filtering process for decreasing the pixel value of the pixel corresponding to the minimum value based on the set amount of blurring corresponding to the depth of the pixel corresponding to the minimum value.

18. The method of claim 11, wherein the step d) further comprises:
setting the amount of blurring corresponding to the spreading of the ultrasound beam and a scan conversion according to the depth for the at least ultrasound image based on the extracted beam profile and image enlargement ratio information indicating an ultrasound image enlargement ratio by the scan conversion.

19. The method of claim 18, wherein the step d) comprises:
multiplying the extracted beam profile with the image enlargement ratio information according to the depth for the at least ultrasound image to set the amount of blurring.

* * * * *